United States Patent [19]

Weinstein

[11] Patent Number: 4,931,571

[45] Date of Patent: Jun. 5, 1990

[54] PROCESS FOR PREPARING ALKYLENE CARBONATES FROM ALKYLENE OXIDES

[75] Inventor: Robert M. Weinstein, Geneva, Switzerland

[73] Assignee: Scientific Design Company, Inc., Little Ferry, N.J.

[21] Appl. No.: 335,379

[22] Filed: Apr. 10, 1989

Related U.S. Application Data

[62] Division of Ser. No. 664,728, Oct. 25, 1984, Pat. No. 4,851,555.

[51] Int. Cl.$^5$ ............................................. C07D 317/12
[52] U.S. Cl. ...................................................... 549/230
[58] Field of Search ........................................... 549/230

[56] References Cited

U.S. PATENT DOCUMENTS

| | | | |
|---|---|---|---|
| 2,766,258 | 10/1956 | Malkemus | 260/340.2 |
| 2,873,282 | 2/1959 | McClellan | 260/340.2 |
| 3,025,305 | 3/1962 | Verdol | 260/340.2 |
| 3,297,634 | 1/1967 | Oxenrider et al. | 260/47 |
| 3,535,342 | 10/1970 | Emmons | 260/340.2 |
| 4,226,778 | 10/1980 | Venturello et al. | 260/340.2 |
| 4,841,072 | 6/1989 | Harvey | 549/230 |

FOREIGN PATENT DOCUMENTS

| | | | |
|---|---|---|---|
| 84992 | 4/1968 | Bulgaria . | |
| 2113207 | 8/1983 | United Kingdom | 549/230 |

*Primary Examiner*—Glennon H. Hollrah
*Assistant Examiner*—Amelia A. Owens
*Attorney, Agent, or Firm*—Kenneth H. Johnson

[57] ABSTRACT

An alkylene oxide, e.g. ethylene oxide, is prepared from the corresponding alkylene carbonate, e.g. ethylene carbonate, in the presence of an effective amount of a quaternary arsonium halide. The quaternary arsonium halides are also effective catalysts for the reverse reaction, that is, to form alkylene carbonates from the corresponding epoxide and carbon dioxide.

3 Claims, No Drawings

PROCESS FOR PREPARING ALKYLENE CARBONATES FROM ALKYLENE OXIDES

This application is a division of U.S. Ser. No. 06/664,728.

PRIOR ART

This invention relates to the preparation of alkylene oxides. Such compounds may be formed by reacting hydrocarbons with oxygen by processes well known in the art. However, there are advantages to forming alkylene oxides by decomposing the corresponding alkylene carbonates, which are generally easier and less hazardous to handle and transport. The present invention relates to such a process and a new class of catalysts, which may be used to decompose alkylene carbonates, particularly ethylene carbonate, to the corresponding epoxide or, alternatively, to prepare alkylene carbonates by the reverse reaction.

While the formation of alkylene oxides from the corresponding olefins has been extensively discussed in the art, the decomposition of alkylene carbonates to form the corresponding epoxides has not.

In U.S. Pat. No. 2,851,469 it is suggested that ethylene carbonate can be decomposed by heating, although large amounts of polymer are said to be formed. Certain catalysts are said to have been suggested, but found unsatisfactory. Using polyhalogenated hydrocarbons is disclosed to give better results.

In U.S. Pat. No. 4,069,234 (and the related U.S. Pat. Nos. 4,111,965; 4,192,810; 4,257,966; and 4,276,223) vicinal epoxides are in the presence of various catalysts, including phosphonium halides, sulfonium halides, sulfoxonium halides, and salts of iron, tin, manganese, and zinc.

The alkali metal halides are used as catalysts from decomposing alkyl-substituted ethylene carbonates in U.S. Pat. No. 4,371,704. A distinction was made between the reactivity of ethylene carbonate and substituted ethylene carbonates. Also, U.S. Pat. No. 4,374,259 discloses tin catalysts for decomposing substituted carbonates, while U.S. Pat. No. 4,265,821 shows the use of lanthanum iodides.

In European Patent Application No. 47,474, a stream of inert gas was used to strip the epoxides formed, while in a related application, EP No. 47,473, a vacuum was used. No new catalysts were disclosed, but phosphonium halides or alkali metal halides were mentioned as being suitable.

Arsonium compounds have been suggested as catalysts for polycarbonate preparation and in heterogeneous reactions (phase transfer catalysis). They have been included in a list of quaternary-onium bicarbonates in the U.S. Pat. No. 4,226,778, which are reported to be useful for making alkylene carbonates from the corresponding halohydrins.

It has now been found that quaternary arsonium compounds may be used to prepare alkylene oxides from the corresponding carbonates or, alternatively, to prepare alkylene carbonates from the corresponding epoxides, as will be seen from the following discussion.

SUMMARY OF THE INVENTION

A process for the preparation of alkylene oxides, e.g., ethylene oxide, from the corresponding alkylene carbonate, which employs as a catalyst an effective amount of a quaternary arsonium halide. Such compounds may be generally defined by the formula $R_1R_2R_3R_4AsX$, where $R_1R_2R_3R_4$ may be hydrogen, alkyl, cycloalkyl, aryl, alkenyl, cycloalkenyl, and may be the same or different. X is either chlorine, bromine, or iodine. A particularly preferred species is tetraphenyl arsonium iodide. In general, the catalyst will be present as about 0.001 to 0.1 mol for each mol of alkylene carbonate. The reaction will be carried out at a temperature of about 100° to 250° C. and a pressure of about 0.005 to 2.0 bar. Where ethylene carbonate is being decomposed, the temperature will be about 150° to 225° C., and the pressure about 0.005 to 2.0 bar.

The organic arsonium halides are also effective as catalysts for the reverse reaction, that is, preparing alkylene carbonates from the corresponding epoxide and carbon dioxide.

DESCRIPTION OF THE PREFERRED EMBODIMENTS

Alkylene carbonates generally may be characterized as high boiling liquids of low toxicity. Of particular importance are ethylene carbonate and propylene carbonate since they may be used as liquid sources of the corresponding oxides, which are quite volatile at ambient conditions. Efficient decomposition of alkylene carbonates to their oxides would be necessary for commercial applications. In the following discussion most attention will be given to the preparation of ethylene oxide from its carbonate, but without intending to limit the scope of the invention.

Decomposition of an alkylene carbonate may be carried out at temperatures generally in the range of 100° to 250° C. For ethylene carbonate, temperatures of 150° to 225° C. are preferred. The pressures should be relatively low in order to favor the decomposition reaction, which produces carbon dioxide. However, pressures in the range of 0.005 to 2.0 bar are feasible. For ethylene carbonate, a pressure between 0.005 and 2.0 bar is preferred. The decomposition reaction may be carried out batchwise or continuously in suitable equipment familiar to those skilled in the art. It may be advantageous to employ a high-boiling solvent, such as sulfolane, or a substituted alkylbenzene (e.g., 1,2,3,4 tetramethyl benzene).

An important aspect of the process is the selection and use of a catalyst from the quaternary arsonium halide group. Broadly, the group includes compounds having the formula $R_1R_2R_3R_4 AsX$, where $R_1R_2R_3R_4$ may be hydrogen, alkyl, cycloalkyl, aryl, alkenyl, or cycloalkenyl, and may be the same or different. X is either chlorine, bromine, or iodine. Examples of such compounds are tetrabutyl arsonium iodide, triphenyl methyl arsonium bromide, triphenyl methyl arsonium iodide, triphenyl heptyl arsonium iodide, tetraphenyl arsonium chloride, tetraphenyl arsonium bromide, or tetraphenyl arsonium iodide. As will be seen, tetraphenyl arsonium iodide ($Ph_4AsI$) has been found particularly useful.

The amount of the quaternary arsonium halide will be chosen to provide the optimum catalytic effect. Generally, this will be between about 0.1 and 10 mol percent relative to the alkylene carbonate. For ethylene carbonate, 0.2 to 5 mol percent is preferred.

The following examples will illustrate the general use-fulness of the process and by comparative examples demonstrate the advantages to be obtained.

EXAMPLES 1

Several quaternary arsonium halides were compared by decomposing ethylene carbonate in a 50-ml round-bottomed flask. Ethylene carbonate was placed in the flask, along with about 0.84 mol percent of the arsonium halide to be tested. Nitrogen was introduced above the decomposing liquid to the flask at a low rate to facilitate removal of the ethylene oxide.

Two methods of analyzing the gaseous reaction products were employed. In Method A, ethylene oxide was measured by passing the gases through a standardized $MgCl_2$/HCl solution, and back-titrating the unreacted HCl with standard NaOH to obtain a measurement of the amount of HCl which was used. This number of moles of reacted HCl is equal to the amount of ethylene oxide produced. Acetaldehyde was measured by gas chromatography via gas sampling of the reaction products prior to entering the $MgCl_2$/HCl scrubber solution.

In Method B, the gaseous reaction products were scrubbed into methanol which was chilled to 0° C. The methanolic solution of ethylene oxide and acetaldehyde so obtained was weighed and analyzed by gas chromatography.

Carbon dioxide could be measured by adsorption on Ascarite (trademark of the Arthur H. Thomas Co.), and the reaction bottoms were also analyzed by gas chromatography.

As the reaction proceeded, ethylene carbonate was added periodically to approximate a continuous reaction in which the ratio of ethylene carbonate to catalyst remains constant. The results of the test are given in Table I following.

TABLE I

| Catalyst | Temp, °C. | Reaction Time, hrs | Yield of EO (f) % (e) |
| --- | --- | --- | --- |
| (a) $Ph_4AsCl.H_2O$ | 163–167 | 13 | 26 |
| (b) $Ph_4AsCl$ | 162–167 | 6.75 | 29 |
| (c) $Ph_4AsI$ | 163–166 | 19 | 98 |
| (d) $Ph_4AsBr$ | 165–170 | 12 | 48 |

(a) Tetraphenyl arsonium chloride monohydrate
(b) Tetraphenyl arsonium chloride (anhydrous)
(c) Tetraphenyl arsonium iodide
(d) Tetraphenyl arsonium bromide
(e) Low yields of EO reflect significant production of polymers
(f) Yield of EO was based on Mol EC charged Since the hydrocarbon moieties are the same, the superior performance of the iodide over the other halides is evident, although they all act as catalysts for the reaction An advantage for using arsonium halide catalysts of the invention is the relatively low make of acetaldehyde, as shown in the following example.

EXAMPLE 2

Experiments following the procedures of Example 1 were carried out to compare quaternary phosphonium halide catalysts with quaternary arsonium halide catalysts. The results are shown in Table II.

TABLE II

| Catalyst | | | Acetaldehyde |
| --- | --- | --- | --- |
| Type | Mol % | Temp, °C. | ppm (d) |
| (a) $Ph_3MePI$ | 2.5 | 164–168 | avg 34,000 |
| (b) $Ph_3MeAsI$ | 2.5 | 164–167 | avg 20,000 |
| (c) $Ph_4AsI$ | 0.85 | 163–165 | 4,800 |
| (c) $Ph_4AsI$ | 0.83 | 178–181 | 5,000 |
| (c) $Ph_4AsI$ | 2.5 | 179–181 | 7,000 |

(a) Triphenyl methyl phosphonium iodide
(b) Triphenyl methyl arsonium iodide
(c) Tetraphenyl arsonium iodide
(d) Based on ethylene oxide, ((wt. AcH/wt. EC) $\times 10^6$)

It can be seen that arsonium halides produce significantly less of the undesirable acetaldehyde; also, that tetraphenyl arsonium halides reduce the acetaldehyde production substantially compared to the triphenyl methyl arsonium halides. Accordingly, tetraphenyl arsonium iodide is a particularly preferred catalyst for the decomposition of ethylene carbonate. It has additional practical advantages which make it particularly suitable for commercial applications. It is thermally stable and can be easily isolated from any heavy reaction products or the alkylene carbonate for reuse, since it is insoluble in water.

Organic antimony halides have been suggested as catalysts for the formation of ethylene carbonate from ethylene oxide and carbon dioxide. However, such compounds appear to be inferior for the decomposition of ethylene carbonate, as will be seen in the following example.

EXAMPLE 3

Comparative

Two organic antimony halides were tested following the procedures of Example 1, except that ethylene carbonate was not added to replace that already consumed; that is, the reaction was carried out batchwise and the relative concentration of the catalyst therefore increased as the ethylene carbonate was decomposed. When 2.5 mol % triphenyl antimony dichloride was used, after 2 hours at 170° C. the ethylene carbonate was found to have been completely polymerized. However, the same amount of tetraphenyl antimony bromide, after 2.25 hours at 173°–8° C., decomposed 94% of the ethylene carbonate, but with a selectivity to ethylene oxide of only 42%. At a lower temperature, 125°–9° C., after 3 hours the same amount of tetraphenyl antimony bromide had only converted 7% of the ethylene carbonate, again with only a low selectivity to ethylene oxide, 53%. A 40% selectivity to acetaldehyde was measured in both cases when tetraphenyl antimony bromide was used.

EXAMPLE 4

An experiment following the procedure of Example 1 was carried out to demonstrate the use of tetraphenyl arsonium iodide ($Ph_4AsI$) to catalyze the decomposition of substituted alkylene carbonates to substituted alkylene oxides.

Propylene carbonate (83.3 g, 0.816 mol) and tetraphenyl arsonium iodide (10.0 g, 0.0196 mol) were placed in a 250-cc, round-bottomed flask. A reaction temperature of 195°±3° C. was employed to decompose propylene carbonate. After 2.75 hours, 24.7% of the propylene carbonate charged was found to have decomposed to a mixture of propylene oxide, allylalcohol, acetone, and propionaldehyde, with selectivities of 87.3%, 0.1%, 1.0% and 1.1%, respectively.

EXAMPLE 5

Arsonium halides will also catalyze the formation of alkylene carbonates. Two experiments were performed, one in the presence of 22 mol % $H_2O$, the other in an anhydrous system.

These experiments were conducted in a 1-liter autoclave to which enough tetraphenyl arsonium iodide had been added to equal 0.25 mol % of the ethylene oxide charged. Ethylene oxide was charged to a 250-cc stainless steel bomb and attached to the autoclave. It was forced into the autoclave by applying a carbon dioxide overpressure, thus adding carbon dioxide and ethylene oxide to the autoclave together. At room temperature, carbon dioxide was added to bring the initial pressure to 28.6 bar, and the reaction was begun by heating to 150°±3° C. A maximum reactor pressure at 150° C. of 52.7 bar was obtained, and after 45 minutes, this pressure was 42.4 bar. Carbon dioxide was then continually added to the autoclave to maintain this pressure. After a 2-hour reaction period, the reactor was cooled and vented through $MgCl_2$/HCl scrubbers in order to trap any unreacted ethylene oxide.

The following table summarizes the results of these experiments.

TABLE III

| | Tetraphenyl Arsonium Iodide Catalyzed Carbonation of Ethylene Oxide | | | |
|---|---|---|---|---|
| Exp. | Charge | % EO (a) Conversion | % EC (b) Selectivity | % MEG (c) Selectivity |
| 1 | 2.31 mol EO/0.5 mol $H_2O$ | 74.80 | 88.10 | 5.19 |
| 2 | 2.22 mol EO | 84.80 | 91.40 | 0.70 |

(a) Ethylene oxide
(b) Ethylene carbonate
(c) Monoethylene glycol

The reaction of alkylene oxides with carbon dioxide to form alkylene carbonates over quaternary arsonium halide catalysts may be carried out at temperatures above about 20° C., particularly above 90° C., preferably in the range of 90° to 200° C. The pressure will be in the range of about 10 -200 bar, preferably 30-80 bar. The molar ratio of carbon dioxide to alkylene oxide should be at least 1/1 and the partial pressure of carbon dioxide should be sufficient to provide the desired selectivity to alkylene carbonate. The amount of catalyst used may be up to about 0.1 mol per mol of alkylene oxide, preferably about 0.001 to 0.02. As the data indicate, the reaction may be carried out with or without water being present, while maintaining a high selectivity to the carbonate.

What is claimed is:

1. A process for the preparation of an alkylene carbonate comprising reacting the corresponding alkylene oxide with carbon dioxide in the presence of an effective amount of a quaternary arsonium halide.

2. The process of claim 1 wherein said quaternary arsonium halide is expressed as $R_1R_2R_3R_4$ AsX, where R is a member of the group consisting of hydrogen, alkyl, cycloalkyl, aryl, alkenyl, and cycloalkenyl, and may be the same or different; and where X is a member of the group consisting of chlorine, bromine, and iodine.

3. The process of claim 1 wherein said quaternary arsonium halide is tetraphenyl arsonium iodide.

* * * * *